United States Patent
Nakajima

(10) Patent No.: US 10,959,614 B2
(45) Date of Patent: Mar. 30, 2021

(54) OPHTHALMOLOGIC DEVICE AND PUPIL STATE MEASURING METHOD

(71) Applicant: TOPCON CORPORATION, Tokyo (JP)

(72) Inventor: Masashi Nakajima, Tokyo (JP)

(73) Assignee: TOPCON CORPORATION, Tokyo (JP)

(*) Notice: Subject to any disclaimer, the term of this patent is extended or adjusted under 35 U.S.C. 154(b) by 117 days.

(21) Appl. No.: 16/144,842

(22) Filed: Sep. 27, 2018

(65) Prior Publication Data
US 2019/0090736 A1  Mar. 28, 2019

(30) Foreign Application Priority Data

Sep. 28, 2017 (JP) .............................. JP2017-188459

(51) Int. Cl.
*A61B 3/14* (2006.01)
*A61B 3/113* (2006.01)
(Continued)

(52) U.S. Cl.
CPC .............. *A61B 3/112* (2013.01); *A61B 3/103* (2013.01); *A61B 3/113* (2013.01); *A61B 3/117* (2013.01); *A61B 3/14* (2013.01)

(58) Field of Classification Search
CPC ........... A61B 3/14; A61B 3/152; A61B 3/102; A61B 3/0083; A61B 3/0041; A61B 3/0058; A61B 3/117; A61B 3/0008; A61B 3/107; A61B 3/12; A61B 3/0075; A61B 3/1173; A61B 3/18; A61B 3/0025; A61B 3/103; A61B 3/0033; A61B 3/165; A61B 3/10; A61B 3/1005; A61B 3/1035; A61B 3/112;
(Continued)

(56) References Cited

U.S. PATENT DOCUMENTS

2004/0156019 A1  8/2004 Masaki
2006/0170865 A1  8/2006 Hirohara et al.
(Continued)

FOREIGN PATENT DOCUMENTS

JP  2006263082 A  10/2006

OTHER PUBLICATIONS

Extended Search Report issued in European Application 18197078. 1-1124 dated Mar. 6, 2019.

*Primary Examiner* — Brandi N Thomas
(74) *Attorney, Agent, or Firm* — Xsensus LLP

(57) ABSTRACT

To provide an ophthalmologic device and a pupil state measuring method capable of securing accuracy of a measurement result of objective measurement and effective for investigating the cause of an error during objective measurement. A pupil state measuring method according to the present invention includes: an ocular characteristic measuring step of objectively measuring an ocular characteristic of a subject eye of a subject; an imaging step of substantially simultaneously imaging an anterior ocular segment of the subject eye from different directions using at least two imaging units in measuring the ocular characteristic; a measuring step of analyzing at least one image of images taken by the at least two imaging units to measure a pupil state of the subject eye; and a step of performing the imaging step and the measuring step in measuring the ocular characteristic.

16 Claims, 8 Drawing Sheets

(51) Int. Cl.
*A61B 3/117* (2006.01)
*A61B 3/11* (2006.01)
*A61B 3/103* (2006.01)

(58) Field of Classification Search
CPC ......... A61B 3/1225; A61B 3/145; A61B 3/15; A61B 3/154; A61B 3/185; A61B 3/11; A61B 3/13; A61B 3/132; A61B 3/135; A61B 3/16; A61F 2009/00851; A61F 2009/00887; A61F 2/16; A61F 9/008; A61F 2240/008; A61F 2/1618; A61F 2009/00846; A61F 2009/00872; A61F 2009/0088; A61F 2/142; A61F 2/1613; A61F 9/00804; A61F 9/00817; G06T 2207/10012; G06T 2207/20008; G06T 2207/20061; G06T 2207/30201; G06T 3/40; G06T 3/60; G06T 5/002; G06T 7/13; G06T 7/337; G06T 7/74; G06T 7/77; G06T 2207/30041; G06T 7/70; G06T 19/006; G06T 3/0093; G06T 7/0012; G06T 7/246; G06T 7/50; G06T 7/73; G06T 7/90; G06T 15/02; G06T 19/20; G06T 2219/2016; G06T 7/64; G06T 7/75
USPC ........ 351/200, 205–206, 209–211, 221–223, 351/243–246
See application file for complete search history.

(56) References Cited

U.S. PATENT DOCUMENTS

| | | |
|---|---|---|
| 2006/0215112 A1 | 9/2006 | Nishio et al. |
| 2016/0150952 A1* | 6/2016 | Raymond ........... A61F 9/00804 351/205 |
| 2016/0345822 A1 | 12/2016 | Fujimura et al. |
| 2017/0100033 A1* | 4/2017 | Sakurada ............. A61B 3/0025 |
| 2018/0199876 A1* | 7/2018 | Liu ........................ A61B 3/11 |

\* cited by examiner

OPHTHALMOLOGIC DEVICE AND PUPIL STATE MEASURING METHOD

CROSS-REFERENCE TO RELATED APPLICATIONS

The present application claims priority under 35 U.S.C. § 119 to Japanese Patent Application No. 2017-188459, filed on Sep. 28, 2017. The above application is hereby expressly incorporated by reference, in its entirety, into the present application.

BACKGROUND OF THE INVENTION

Field of the Invention

The present invention relates to an ophthalmologic device and a pupil state measuring method, and in particular, relates to an ophthalmologic device and a pupil state measuring method for measuring a pupil state of a subject eye.

Description of the Related Art

Japanese Patent Application Laid-Open No. 2006-263082 (which is hereinafter referred to as Patent Literature 1) discloses an ocular optical characteristic measuring apparatus including an objective ocular refractive power measuring system (30). In Patent Literature 1, an anterior ocular segment image of a subject at a target setting position is acquired by the ocular refractive power measuring system (30) and a photoelectric detector (37), and the pupil diameter of the subject eye is calculated from this anterior ocular segment image. Then, based on this pupil diameter and the like, stop holes for aperture stops of a projection optical system (2) which projects a measurement luminous flux on the subject eye and a light-receiving optical system (3) which receives reflected light from the subject eye are selected, and a visual target image is acquired by a photoelectric detector (21) via the projection optical system (2) and the light-receiving optical system (3) ([0046] to [0057] in Patent Literature 1).

CITATION LIST

Patent Literature 1: Japanese Patent Application Laid-Open No. 2006-263082

SUMMARY OF THE INVENTION

With a conventional ophthalmologic device, when an optical characteristic of a subject eye, such as a refractive power, is objectively measured, a pupil state of the subject eye in the objective measurement has not been able to be measured. There can be a case where a measurement luminous flux is shaded by the iris of the subject eye when miosis (contraction of pupil) arises during objective measurement, and there has been a problem that accuracy of a measurement value cannot be secured when miosis of the subject eye arises in the objective measurement. Furthermore, there can be a case where an error caused by miosis of the subject eye arises during objective measurement, and with the conventional ophthalmologic device, it has been difficult to investigate the cause of the error.

While Patent Literature 1 discloses that the single photoelectric detector (37) performs both measurement of the refractive power of the subject eye and acquisition of the anterior ocular segment image used for calculating the pupil diameter, the single photoelectric detector (37) cannot simultaneously perform measurement of the refractive power of the subject eye and acquisition of the anterior ocular segment image in the measurement of the refractive power.

Notably, Patent Literature 1 discloses that the anterior ocular segment image may be photographed by the projection optical system (2) and the light-receiving optical system (3) (paragraph [0058] in Patent Literature 1). However, when measurement of the refractive power and imaging of the anterior ocular segment are performed using separate optical systems, a plurality of cameras are needed, and there has been a problem that this causes complication of the apparatus, and increase in size and costs.

The present invention is devised in view of such circumstances. The present invention aims to provide an ophthalmologic device and a pupil state measuring method which can secure accuracy of a measurement result of objective measurement and is useful for investigating the cause of an error during objective measurement.

In order to solve the aforementioned problems, there is provided an ophthalmologic device according to a first aspect of the present invention, including: an ocular characteristic measuring unit configured to objectively measure an ocular characteristic of a subject eye of a subject; at least two imaging units configured to substantially simultaneously photograph an anterior ocular segment of the subject eye from different directions during measurement of the ocular characteristic by the ocular characteristic measuring unit; a pupil state measuring unit configured to measure a pupil state of the subject eye base on at least one image of images photographed by the at least two imaging units; and a controlling unit configured to cause the at least two imaging units to photograph the anterior ocular segment of the subject eye, and cause the pupil state measuring unit to measure the pupil state of the subject eye base on the at least one image.

According to the first aspect, since the pupil state during objective measurement can be detected, accuracy of a measurement result of the objective measurement can be secured. Furthermore, according to the first aspect, by measuring the pupil state using two imaging units provided for alignment, it is possible to prevent complication of the device, increase in device size, and increase in costs.

In the first aspect, the ophthalmologic device according to a second aspect of the present invention further includes a distance detecting unit configured to detect a distance between the ocular characteristic measuring unit and the subject eye based on the two imaging units and the photographed images.

In the first or second aspect, the ophthalmologic device according to a third aspect of the present invention further includes a storage unit configured to store a measurement result of the ocular characteristic by the ocular characteristic measuring unit and a measurement result of the pupil state by the pupil state measuring unit.

According to the third aspect, an optometrist (for example, an ophthalmologist, a nurse, an orthoptist, or the like) can refer to the pupil state during objective measurement stored in the storage unit in analyzing the measurement result of the ocular characteristic. Thereby, the cause of error occurrence in ocular characteristic measurement can be investigated, and accuracy of the measurement result can be secured.

In any of the first to third aspects, there is provided the ophthalmologic device according to a fourth aspect of the present invention, wherein the pupil state measuring unit measures, as the pupil state, at least one of a diameter of a pupil of the subject eye in each longitudinal direction and an eccentric amount of the pupil relative to a corneal apex of the subject eye.

In any of the first to fourth aspects, there is provided the ophthalmologic device according to a fifth aspect of the present invention, wherein, during measurement of the ocular characteristic by the ocular characteristic measuring unit, the controlling unit controls to perform photographing of the anterior ocular segment of the subject eye by the at least two imaging units and measurement of the pupil state of the subject eye based on the at least one image of the images photographed by the at least two imaging units.

According to the fifth aspect, change of the pupil state over time in measuring the ocular characteristic can be measured.

In any of the first to fifth aspects, the ophthalmologic device according to a sixth aspect of the present invention further includes: a determining unit configured to determine whether to issue a report regarding the pupil state or not, based on the pupil state of the subject eye during measurement of the ocular characteristic by the ocular characteristic measuring unit; and a reporting unit configured to issue the report when the determining unit determines to issue the report.

In the sixth aspect, there is provided the ophthalmologic device according to a seventh aspect of the present invention, wherein the determining unit determines to issue the report when a pupil diameter measured by the pupil state measuring unit in at least one longitudinal direction, is not more than a first threshold determined from a diameter of a measurement luminous flux.

In the sixth or seventh aspect, there is provided the ophthalmologic device according to an eighth aspect of the present invention, wherein the determining unit determines to issue the report when a displacement of a center position of a pupil of the subject eye relative to an alignment reference position of the pupil of the subject eye, the displacement being measured by the pupil state measuring unit, is not less than a second threshold determined from the diameter of the measurement luminous flux.

In any of the first to eighth aspects, the ophthalmologic device according to a ninth aspect of the present invention further includes a determining unit configured to determine whether or not to perform measurement based on a pupil diameter of the subject eye before starting of the measurement of the ocular characteristic by the ocular characteristic measuring unit, wherein the controlling unit stops the measurement of the ocular characteristic by the ocular characteristic measuring unit.

In the ninth aspect, the ophthalmologic device according to a tenth aspect of the present invention further includes a reporting unit configured to report that the measurement is stopped when the determining unit determines to stop the measurement.

There is provided a pupil state measuring method according to an eleventh aspect of the present invention, including: an ocular characteristic measuring step of objectively measuring an ocular characteristic of a subject eye of a subject; a photographing step of substantially simultaneously photographing an anterior ocular segment of the subject eye from different directions using at least two imaging units during measurement of the ocular characteristic; a measuring step of analyzing at least one image of images photographed by the at least two imaging units to measure a pupil state of the subject eye; and a step of performing the photographing step and the measuring step during the measurement of the ocular characteristic.

In the eleventh aspect, the pupil state measuring method according to a twelfth aspect of the present invention further includes storing step of storing a measurement result of the ocular characteristic and a measurement result of the pupil state in a storage unit.

In the eleventh or twelfth aspect, there is provided the pupil state measuring method according to a thirteenth aspect of the present invention, the photographing step and the measuring step are repeatedly performed during the measurement of the ocular characteristic.

According to the present invention, since the pupil state during objective measurement can be detected, accuracy of a measurement result of the objective measurement can be secured. Furthermore, according to the present invention, by measuring the pupil state using two imaging units provided for alignment, it is possible to prevent complexation of the device, increase in device size and increase in costs.

DETAILED DESCRIPTION OF THE PREFERRED EMBODIMENTS

Hereafter, embodiments of an ophthalmologic device and a pupil state measuring method according to the present invention are described in accordance with the accompanying drawings.

Outline of Ophthalmologic Device

Figure 1:
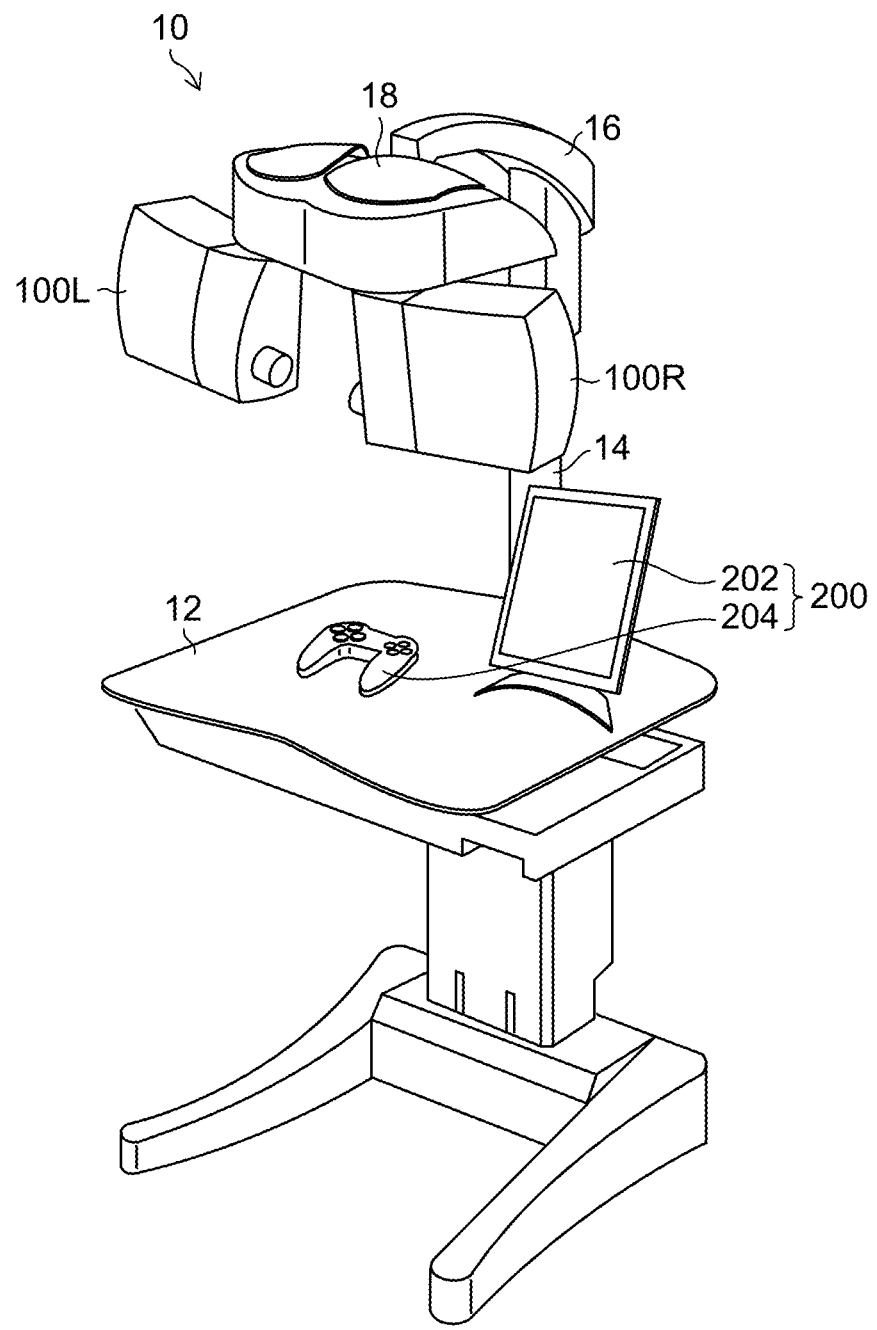
FIG. 1 is an appearance view showing an ophthalmologic device according to an embodiment of the present invention.

FIG. 1 is an appearance view showing an ophthalmologic device according to an embodiment of the present invention.

An ophthalmologic device 10 according to the present embodiment is a device which can perform both objective measurement and subjective optometry on the eyes of a subject with an optometry unit 100 (100L and 100R). In the following description, the subject and an optometrist are also referred to as "operators".

As shown in FIG. 1, the ophthalmologic device 10 according to the present embodiment includes an optometry table 12, the optometry unit 100 (100L and 100R) and a user interface (UI) 200.

The optometry table 12 is a table adjustable in height depending on the body build and the like of the subject.

Onto the optometry table 12, a pillar-shaped supporting part 14 is attached substantially perpendicularly to the surface of the optometry table 12. The supporting part 14 is expandably and shrinkably configured. By expanding and shrinking the supporting part 14 in accordance with the body build and the like of the subject, the height of the optometry units 100L and 100R can be adjusted.

An arm part 16 is attached to the upper end part of the supporting part 14. The arm part 16 is rotatable around the supporting part 14. A hanging part 18 is attached to the arm part 16, and the optometry units 100L and 100R are hung on the hanging part 18. A subject or an optometrist can rotate the optometry units 100L and 100R relative to the supporting part 14, and thereby, the optometry units 100L and 100R can be made right opposite to the subject.

The hanging part 18 includes a first driving unit 20 (see FIG. 3) therein for moving the optometry units 100L and 100R. An operator operates the first driving unit 20 using the UI 200, and thereby, can move the optometry units 100L and 100R. With the first driving unit 20, the operator can adjust the angle and the distance between the optometry units 100L and 100R in accordance with the positions of and the distance between the right and left eyes of the subject.

The optometry units 100 (100L and 100R) include respective optical systems for measuring and inspecting the right and left eyes of the subject, and has binocular simultaneous objective refractivity measurement and subjective optometry functions. When the subject allows its face to be supported on a face supporting part 24 (see FIG. 3), the right and left subject eyes are made right opposite to optometry windows of the optometry units 100L and 100R, and various kinds of measurement can be performed.

The UI 200 includes an operating unit for receiving operation input from the operator, and a displaying unit for displaying a measurement result by the ophthalmologic device 10. In the example shown in FIG. 1, a touch panel display 202 and a controller 204 are illustrated as the UI 200.

The touch panel display 202 includes a display screen on which a graphical user interface (GUI) for receiving operation, the measurement result by the ophthalmologic device 10, and the like are displayed, and on the surface of the display screen, a touch panel for receiving operation of the operator is provided. The touch panel may be in any type such as a matrix switch type, a resistive layer type, a surface acoustic wave type, an infrared ray type, an electromagnetic induction type and a capacitance type.

The controller 204 includes operating members (operating buttons, switches and the like) for receiving operation from the operator.

Here, the type of the UI 200 is not limited to the touch panel display 202 or the controller 204. In place of these or in addition to these, the UI 200 may include a pointing device such as a mouse, a keyboard for inputting characters, and the like.

Next, a configuration of the optometry units 100L and 100R according to the present embodiment is described. Here, since the optometry units 100L and 100R are in horizontal symmetry, the optometry unit 100R for the right eye is hereafter described, and description of the optometry unit 100L for the left eye is omitted.

Figure 2:
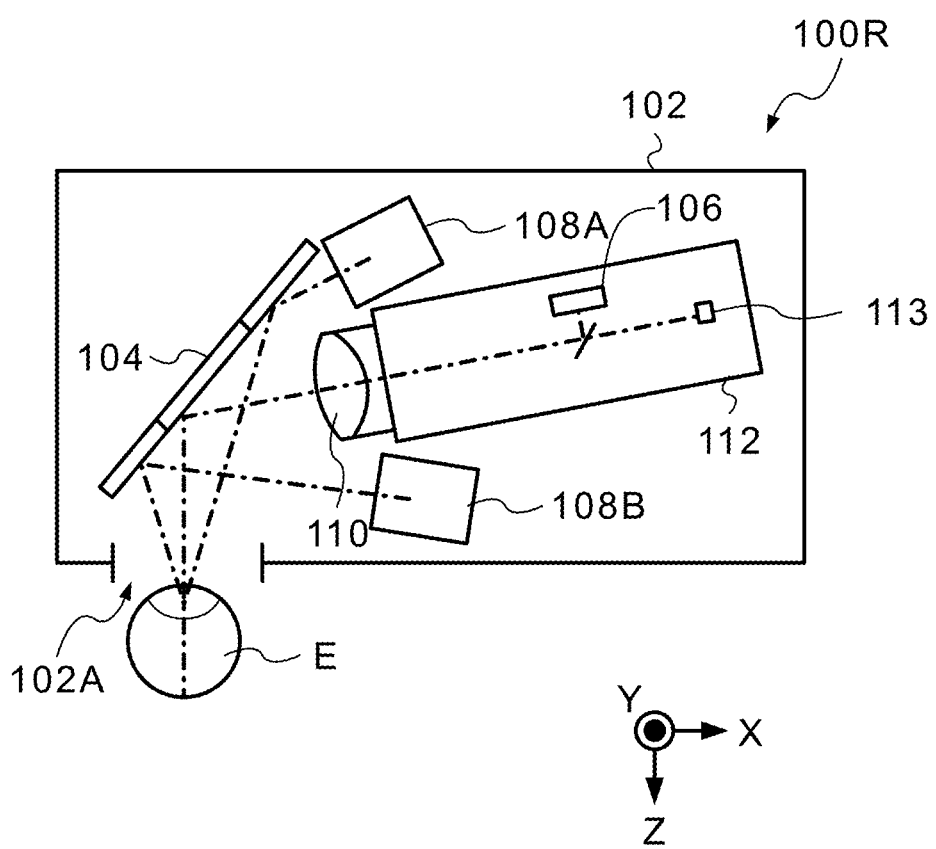
FIG. 2 is a diagram showing an optical system of an optometry unit according to the embodiment.

FIG. 2 is a diagram showing an optical system of the optometry unit 100R according to the present embodiment. In the following description, a three-dimensional Cartesian coordinate system is used in which an X-direction is the horizontal direction (transverse direction), a Y-direction is the vertical direction (longitudinal direction), and a Z-direction is the direction perpendicular to the XY-directions. Herein, the Z-direction substantially coincides with a sight direction (gaze direction).

As shown in FIG. 2, the optometry unit 100R includes a mirror (deflection member) 104, an alignment optical system 106, a stereo camera 108 (cameras (imaging units) 108A and 108B), an objective lens 110 and a measurement optical system 112. These constituents are contained in an optometry unit casing 102.

A substantially circular optometry window 102A is formed in the optometry unit casing 102. Into the optometry window 102A, a plate-shaped member which transmits light (for example, a member relatively high in transmissivity such as a white glass plate) may be fitted.

The mirror 104 (deflection member) is disposed on the far side (−Z-side, minus Z-side) relative to the optometry window 102A. The mirror 104 is disposed so as to be frontally positioned when the subject allows a subject eye E to be right opposite to the optometry window 102A, and is inclined such that the end part on the right side (+X-side, plus X-side) is on the far side (−Z-side) relative to the optometry window 102A. Here, while in the present embodiment, the mirror 104 is used as the deflection member, in place of the mirror 104, an optical member such as a prism which can deflect light may be used.

The alignment optical system 106 is disposed in the measurement optical system 112, and includes a light source (for example, a light-emitting diode (LED)), and a transmitter lens. Light emitted from this light source is radiated, as parallel light, onto the mirror 104 through the objective lens 110. The light radiated onto the mirror 104 is reflected on the mirror 104, and is radiated onto the subject eye E. Thereby, an alignment index image is projected on the subject eye E.

The stereo camera 108 includes two or more cameras attached to different places in the optometry unit 100R. It substantially simultaneously photographs an anterior ocular segment of the subject eye E from different directions. By analyzing positions of feature points (feature sites) in two or more anterior ocular segment images photographed by the stereo camera 108, positional relation between the subject eye E and the optometry unit 100R can be obtained, and the optometry unit 100R can be aligned relative to the subject eye E.

While a corneal reflection image (Purkinje image) of an index luminous flux projected on the cornea of the anterior ocular segment is used as the feature point on the anterior ocular segment in the explanation, but the feature point not limited to the explanation. A pupil center or the like may be used as the feature point.

While in the example shown in FIG. 2, the stereo camera 108 includes the two cameras 108A and 108B, the number and the installation places of cameras are not limited to those in the example shown in FIG. 2. One of the cameras 108A and 108B may be disposed in the measurement optical system 112. Moreover, when the stereo camera 108 includes three or more cameras, some of those may be disposed in the measurement optical system 112.

The measurement optical system 112 includes a configuration for measuring characteristics of the subject eye E. In addition to the aforementioned alignment optical system 106, the measurement optical system 112 includes: a projection optical system for projecting a visual target on the subject eye E via the objective lens 110 and the mirror 104, and projecting measurement light on the subject eye E via the objective lens 110 and the mirror 104; and a light-receiving optical system 113 which receives reflected light.

Figure 3:
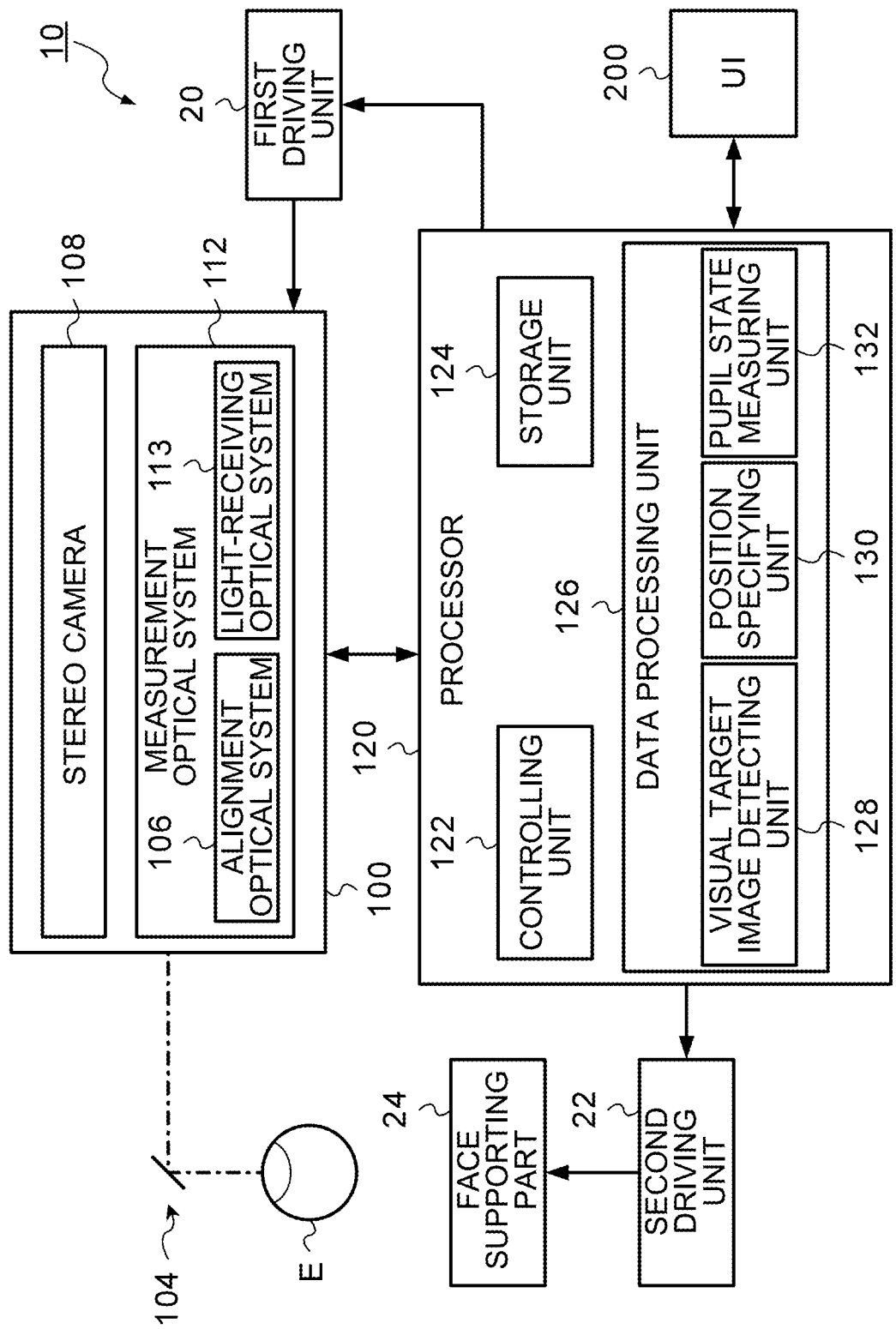
FIG. 3 is a block diagram showing the ophthalmologic device according to the embodiment.

FIG. 3 is a block diagram showing the ophthalmologic device according to the present embodiment.

(Processor 120)

A processor 120 performs various kinds of information processing. In the present specification, the "processor" means a circuit such, for example, as a CPU (Central Processing Unit), a GPU (Graphics Processing Unit), an ASIC (Application Specific Integrated Circuit), or a programmable logic device (for example, an SPLD (Simple Programmable Logic Device), a CPLD (Complex Programmable Logic Device) or an FPGA (Field Programmable Gate Array)).

The processor 120 realizes functions according to the embodiment, for example, by reading and executing a program stored in a storage circuit or a storage device. At least part of the storage circuit or the storage device may be included in the processor 120. Moreover, at least part of the storage circuit or the storage device may be provided outside the processor 120. Processing which can be performed by the processor 120 is mentioned later. The processor 120 includes a controlling unit 122, a storage unit 124 and a data processing unit 126.

(Controlling Unit 122)

The controlling unit 122 performs control of the individual units of the ophthalmologic device 10. In particular, the controlling unit 122 controls the optometry units 100L and 100R, the first driving unit 20, and a second driving unit 22. Control which can be performed by the controlling unit 122 is mentioned later.

(Storage Unit 124)

The storage unit 124 stores therein various kinds of data. For example, as the storage unit 124, a device including a magnetic disk such, for example, as an HDD (Hard Disk Drive), a device including a flash memory such as an eMMC (embedded Multi Media Card) and an SSD (Solid State Drive), or the like can be used. Data stored in the storage unit 124 includes data (measurement data, imaging data and the like) acquired by the light-receiving optical system of the measurement optical system 112, information regarding the subject and the subject eye E, and the like. Various computer programs and data for operating the ophthalmologic device 10 may be stored in the storage unit 124. Various kinds of data used and referred to in the processing mentioned later is stored in the storage unit 124. The storage unit 124 includes the aforementioned storage circuit or storage device.

(Data Processing Unit 126)

The data processing unit 126 performs various kinds of data processing. In particular, the data processing unit 126 analyzes images acquired by the stereo camera 108.

(Optometry Unit 100)

The optometry units 100L and 100R accommodate configurations for measuring and imaging the subject eyes E, and configurations for their preparation. The former includes the measurement optical system, and the latter includes the alignment optical system. The optometry units 100L and 100R may include configurations for performing focusing of the measurement optical system 112, and the like. Moreover, the optometry units 100L and 100R may include light sources (anterior ocular segment illuminating light sources) for lighting the anterior ocular segments of the subject eyes E.

(Measurement Optical System 112)

The measurement optical system 112 (ocular characteristic measuring unit) includes a configuration for measuring a characteristic of the subject eye E. The measurement optical system 112 includes a configuration in accordance with functions which the ophthalmologic device 10 provides (a measurement function, an imaging function and the like). For example, in addition to the aforementioned alignment optical system 106, a light source, optical elements (an optical member; an optical device), an actuator, a mechanism, a circuit, a display device, a light-receiving element, an image sensor and the like are provided in the measurement optical system 112. The configuration of the measurement optical system 112 may be similar to that of a conventional ophthalmologic device. The measurement optical system 112 can project a visual target image on the subject eye E via the objective lens 110 and the mirror 104, project measurement light on the subject eye E via the objective lens 110 and the mirror 104, and receive reflected light by the light-receiving optical system 113. For example, in the case of having a function of objectively measuring ocular refractive power of the subject eye, an optical system of a known refractometer is disposed in the measurement optical system 112.

The measurement optical system 112 may include a configuration for providing an accompanying function with inspection. For example, a fixation optical system which presents a visual target for fixing or fogging the subject eye E may be provided.

(Alignment Optical System 106)

The alignment optical system 106 includes the light source and the transmitter lens, and projects a luminous flux on the subject eye E. The light source included in the alignment optical system 106 is disposed in the measurement optical system 112, projects a parallel luminous flux on the cornea of the subject eye E along the optical axis of the objective lens 110. Thereby, an index for alignment is projected on the cornea of the subject eye E. This index is detected as a virtual image (Purkinje image) due to cornea surface reflection. Alignment using the index at least includes optical axis direction alignment in the optical axis direction of the measurement optical system 112. The alignment using the index may include XY-alignment in the X-direction and the Y-direction.

In the present embodiment, the optical axis of the measurement optical system 112 is bent by the mirror 104. The optical axis of the measurement optical system 112 is configured so as to substantially coincide with the Z-axis at the position of the mirror image of the measurement optical system 112 relative to the mirror 104. The alignment of the measurement optical system 112 in the optical axis direction corresponds to Z-alignment. In the following description, the alignment of the measurement optical system 112 in the optical axis direction is referred to as the Z-alignment.

The Z-alignment is performed by analyzing two or more taken images substantially simultaneously obtained by the stereo camera 108. The XY-alignment is performed by analyzing the two or more taken images obtained by the stereo camera 108.

The XY-alignment is performed based on the positions, in the XY-directions, of Purkinje images (index images) drawn in the two or more taken images. The XY-alignment is performed by manually or automatically moving the optometry unit 100R such that the index image is guided within an allowable range (alignment mark) of displacement in alignment.

In the case of manual alignment, the controlling unit 122 displays the two or more taken images and the alignment mark on the UI 200 (touch panel display 202). An operator operates the UI 200 to move the optometry unit 100R with the first driving unit 20 so as to move the index image within the allowable range (alignment mark) of displacement in alignment.

In the case of automatic alignment, the data processing unit 126 calculates a displacement of the index image relative to the alignment mark. The controlling unit 122 moves the optometry unit 100R in the XY-directions so as to cancel the displacement calculated by the data processing unit 126.

(Stereo Camera 108)

The stereo camera 108 includes two or more cameras attached to different places in the optometry unit 100R. Each camera of the stereo camera 108 is, for example, a video camera which takes moving image at a predetermined frame rate. Each camera receives reflected light by the mirror 104 and substantially simultaneously takes image of the anterior ocular segment of the subject eye E from different directions.

In the example shown in FIG. 2, the two cameras 108A and 108B are provided. Moreover, each of the cameras 108A and 108B is disposed at a position off (shifted from) the optical path of the measurement optical system 112.

Here, the cameras 108A and 108B may be provided below (on the −Y-side of) the optical path of the measurement optical system 112. Thereby, reflected light of a luminous flux (index) projected on the anterior ocular segment (for example, the cornea) of the subject eye E hardly suffers vignetting by eyelashes or eyelids.

While the number of cameras included in the stereo camera 108 may be any number not less than two, there may be a configuration in which the anterior ocular segment of the subject eye E can be substantially simultaneously photographed from two different directions. Moreover, one of the cameras included in the stereo camera 108 may be concentrically disposed with the measurement optical system 112.

Herein, to be "substantially simultaneous" means that a displacement in imaging timing to such an extent that eye movement can be ignored is allowed in imaging with the two or more cameras of the stereo camera 108. By substantially simultaneously imaging the anterior ocular segment of the subject eye E from different directions with the two or more cameras of the stereo camera 108, two or more taken images at the time when the subject eye E is at the same position (orientation) can be acquired.

Moreover, while imaging by the stereo camera 108 may be any of moving picture imaging and still picture imaging, in the present embodiment, the case of performing the moving picture imaging is described. In the case of the moving picture imaging, by performing control of matching in imaging start timing and/or performing control of a frame rate and imaging timing of each frame, with the individual cameras, the anterior ocular segment of the subject eye E can be "substantially simultaneously" photographed. Meanwhile, in the case of the still picture imaging, by performing control of matching in imaging timing for the individual cameras included in the stereo camera 108, with the individual cameras, the anterior ocular segment of the subject eye E can be "substantially simultaneously" photographed.

(Face Supporting Part 24)

The face supporting part 24 includes a member for supporting the face of the subject. For example, the face supporting part 24 includes a forehead receiver which the forehead of the subject comes into contact with, and a chin receiver which the chin of the subject is placed on. Additionally, the face supporting part 24 may include any one of the forehead receiver and the chin receiver, or may include a member other than these.

(First Driving Unit 20 and Second Driving Unit 22)

Upon reception of control by the controlling unit 122, the first driving unit 20 moves the optometry units 100L and 100R. The first driving unit 20 can individually three-dimensionally move the optometry units 100L and 100R. For example, similarly to a conventional one, the first driving unit 20 includes a mechanism for moving the optometry units 100L and 100R in the X-direction, a mechanism for moving them in the Y-direction, and a mechanism for moving them in the Z-direction. Moreover, the first driving unit 20 may include a rotating mechanism which individually rotates the optometry units 100L and 100R in a plane (horizontal plane, vertical plane or the like) including the Z-axis of the optometry units 100L and 100R.

Upon reception of control by the controlling unit 122, the second driving unit 22 moves the face supporting part 24. The second driving unit 22 can three-dimensionally move the face supporting part 24. The second driving unit 22 includes a mechanism for moving the face supporting part 24 which holds, for example, both or at least one of the forehead and the chin of the subject in the X-direction, a mechanism for moving it in the Y-direction, and a mechanism for moving it in the Z-direction. Moreover, the second driving unit 22 may include a rotating mechanism for changing an orientation of the face supporting part 24 (or a member included in it). When a plurality of members are provided in the face supporting part 24, the second driving unit 22 may be configured to individually move these members. For example, the second driving unit 22 may be configured to individually move the forehead receiver and the chin receiver. Additionally, the ophthalmologic device 10 may include any one of the first driving unit 20 and the second driving unit 22, or may include both of these.

The user interface (UI 200) provides functions for transmitting and receiving information between the ophthalmologic device 10 and its user, such as display of information, input of information, and input of an operation instruction. The UI 200 provides an output function and an input function. Examples of a configuration providing the output function include a display device such as a flat panel display, a voice output device, a printing output device, and a data writer which performs writing in a recording medium. Examples of a configuration providing the input function include an operation lever, buttons, keys, a pointing device, a microphone, and a data writer. The UI 200 may include a graphical user interface (GUI) for performing input and output of information.

In the present embodiment, the UI 200 includes the touch panel display 202 in which the output function and input function are integrated, and the controller 204.

(Details of Data Processing Unit 126)

Details of the data processing unit 126 are described. The data processing unit 126 includes an index image detecting unit 128 and a position specifying unit 130.

(Index Image Detecting Unit 128)

The index image detecting unit 128 analyzes two or more taken images substantially simultaneously obtained by the stereo camera 108, and thereby, detects index images drawn in the individual taken images.

When the cameras 108A and 108B take moving images, the index image detecting unit 128 detects the index image from each frame. The index image detecting unit 128 analyzes a pixel value of the taken image, and thereby, detects the index image. When the taken image is a luminance image, the index image detecting unit 128 specifies an image region (pixel) corresponding to the index image on the basis of a distribution of luminance values in the taken image. This processing includes, for example, processing of selecting a pixel having a higher luminance value than a fixed (established) threshold. When the taken image is a color image, the index image detecting unit 128 includes, for example, processing of selecting a pixel having a higher luminance value than the fixed threshold, or processing of selecting a pixel exhibiting a predetermined color.

(Position Specifying Unit 130)

The position specifying unit 130 specifies a position of the subject eye E on the basis of the two or more index images detected from the two or more taken images substantially simultaneously acquired by the stereo camera 108.

The position specifying unit 130 at least calculates the distance between the subject eye E and the measurement optical system 112 in the Z-direction. Based on this calculation result, the Z-alignment is performed. Furthermore, the position specifying unit 130 may calculate displacements between the subject eye E and the measurement optical system 112 in the XY-directions. Based on this calculation result, the XY-alignment is performed.

Next, processing performed by the position specifying unit 130 according to the present embodiment is described with reference to FIG. 4 to FIG. 6.

Figure 4:
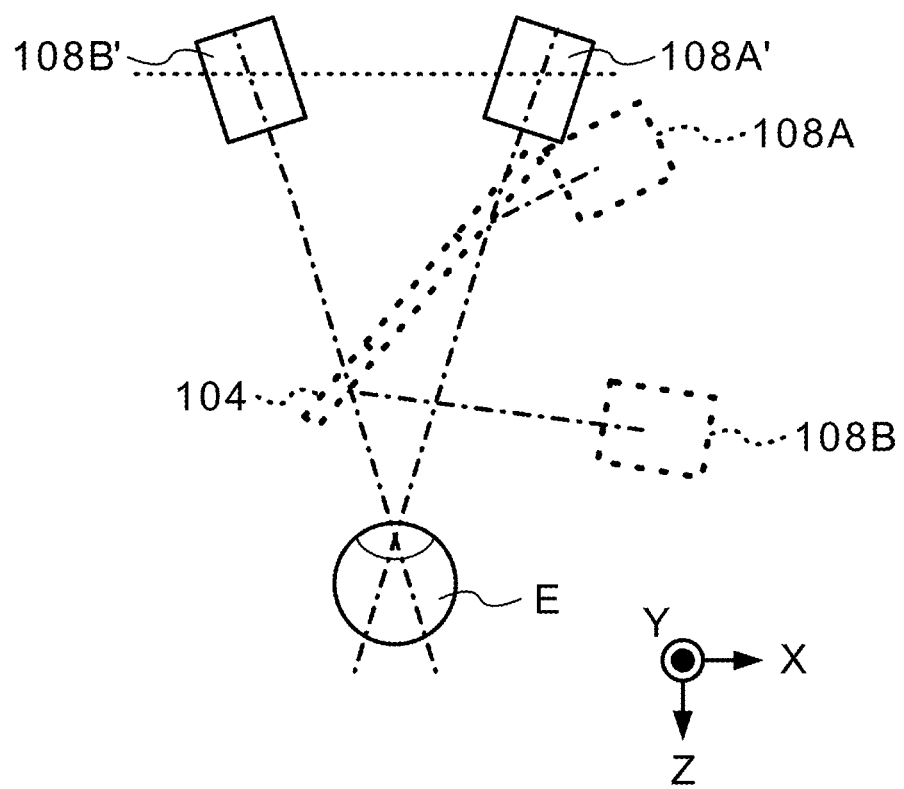
FIG. 4 is a diagram showing a state where mirror reflection transformations are performed on individual stereo cameras relative to a mirror.

FIG. 4 shows a state where mirror reflection transformation is performed on the individual cameras 108A and 108B relative to the mirror 104. Description is hereafter made using the cameras 108A' and 108B' after mirror reflection transformation (mirroring transformation).

Figure 5:
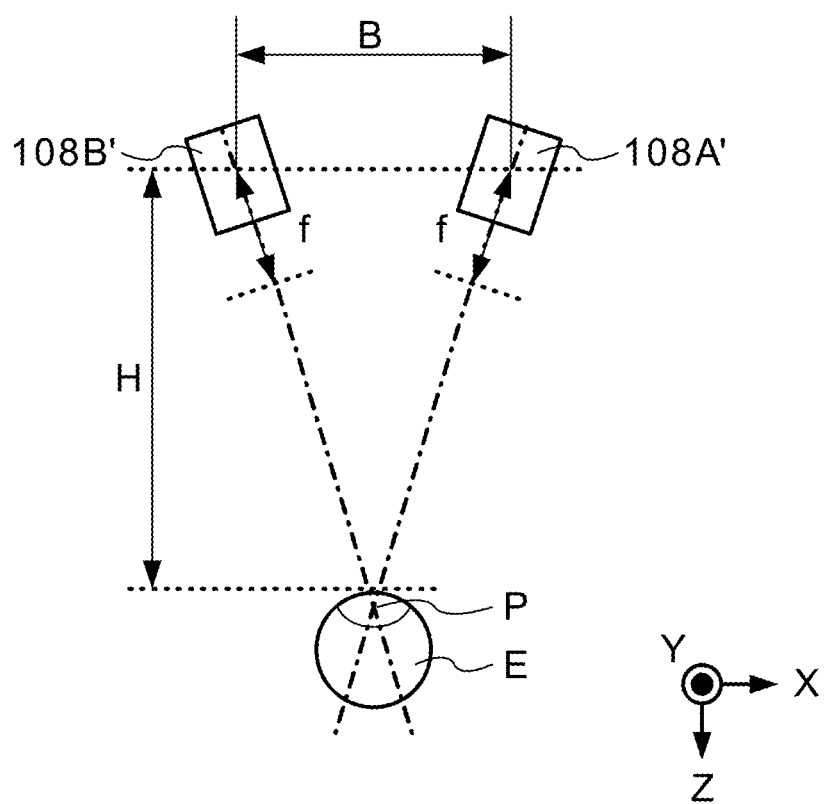
FIG. 5 is a top view showing positional relation between a subject eye and the stereo cameras after the mirror reflection transformations.

FIG. 5 is a top view showing positional relation between the subject eye E and the cameras 108A' and 108B' after mirror reflection transformation. FIG. 6 is a lateral view showing the same.

The distance (base line length) between the cameras 108A' and 108B' in the XY-directions is represented by "B". The distance (index image distance) between the base line of the cameras 108A' and 108B' and an index image P is represented by "H". The distance (screen distance) between each of the cameras 108A' and 108B' and its screen plane is represented by "f". In general, when an index luminous flux is projected on the subject eye E as a parallel luminous flux, the index image (Purkinje image) P is formed at a position displaced, in the +Z-direction, from the cornea surface by a half of the cornea curvature radius of the subject eye E.

In such an arrangement state, resolutions of the taken images by the cameras 108A' and 108B' are indicated by the following expressions. Herein, Δp represents the pixel resolution.

Resolution in the XY-Directions:

$$\Delta XY = H \times \Delta p / f$$

Resolution in the Z-Direction:

$$\Delta Z = H \times H \times \Delta p / (B \times f)$$

Figure 6:
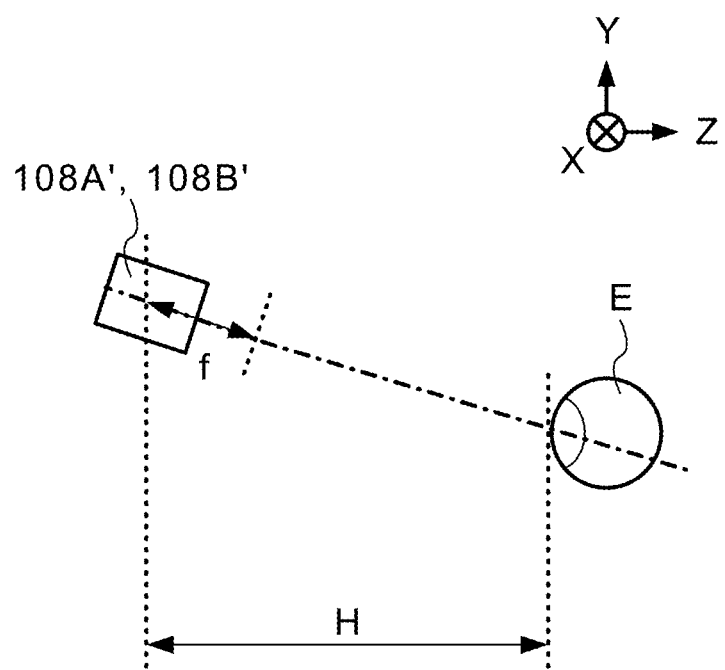
FIG. 6 is a lateral view showing positional relation between the subject eye and the stereo cameras after the mirror reflection transformations.

The position specifying unit 130 applies known triangulation with the arrangement relation shown in FIG. 5 and FIG. 6 taken into consideration, to the positions (known) of the cameras 108A' and 108B' and the positions of the index images P in the two taken images. Thereby, the position specifying unit 130 specifies the position of the index image P, that is, the position of the subject eye E. The specified position at least includes the position in the Z-direction, and may further include the positions in the XY-directions.

The position of the subject eye E specified by the position specifying unit 130 is sent to the controlling unit 122. Based on the Z-position of the subject eye E, the controlling unit 122 controls at least one of the first driving unit 20 and the second driving unit 22 such that the distance between the subject eye E and the measurement optical system 112 in the Z-direction is caused to coincide with a working distance. Furthermore, based on the XY-positions of the subject eye E, the controlling unit 122 controls at least one of the first driving unit 20 and the second driving unit 22 such that the optical axis of the measurement optical system 112 is caused to coincide with the axis of the subject eye E. Here, the working distance means a fixed distance between the subject eye E and the measurement optical system 112 for performing measurement by the measurement optical system 112.

As above, the position specifying unit 130 can obtain the position of the index image P (Purkinje image) as the position (or its approximated position) of the subject eye E. Furthermore, the position specifying unit 130 can obtain the position of the cornea (apex) of the subject eye E on the basis of the specified position of the index image P and the cornea curvature radius which is separately measured. In the state where the alignment is appropriately performed in XYZ directions, it can be considered that the corneal apex is disposed at the position displaced, in the −Z-direction, from the index image P by a half of the cornea curvature radius. Accordingly, by subtracting the value of a half of the cornea curvature radius from the Z-coordinate value of the index image P, the Z-coordinate value of the corneal apex (XYZ-coordinate values including it) can be obtained.

While the cornea curvature radius can be set to be the average cornea curvature r which is 8 mm, an actual value can also be used when the cornea curvature radius of the subject eye can be acquired.

Measurement of the cornea curvature radius is performed using a keratometer or a cornea topographer. When the ophthalmologic device 10 does not include a function of measuring the cornea curvature radius, a measurement value of the cornea curvature radius which was obtained in the past is input to the ophthalmologic device 10. The position specifying unit 130 obtains the corneal apex position using this measurement value. Meanwhile, when the ophthalmologic device 10 includes the function of measuring the cornea curvature radius, the cornea curvature radius can be measured, for example, after performing alignment, and then alignment can be performed again using the obtained measurement value. Moreover, even when the ophthalmologic device 10 includes the function of measuring the cornea curvature radius, the measurement value of the cornea curvature radius which was obtained in the past can also be used.

(Pupil State Measuring Unit 132)

Figure 7:
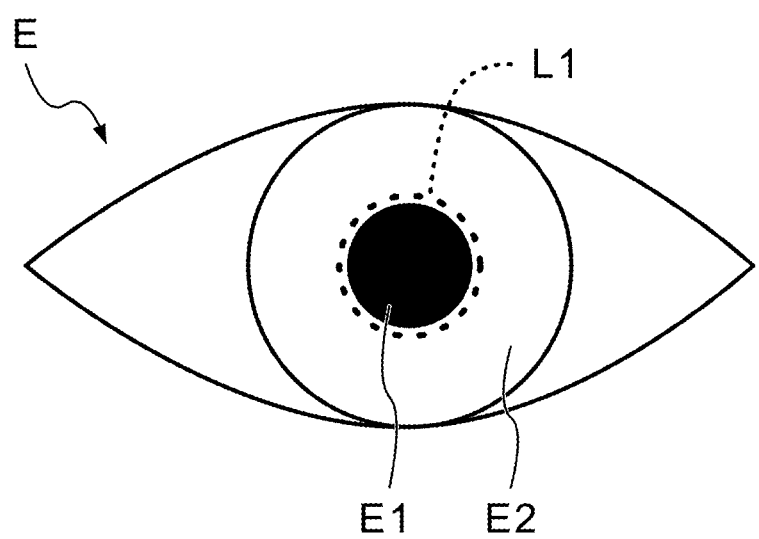
FIG. 7 is a diagram showing an image obtained by imaging the subject eye.

Next, a measuring method of a pupil state is described with reference to FIG. 7. FIG. 7 is a diagram showing an image obtained by photographing the subject eye E.

As shown in FIG. 7, in the present embodiment, first, the pupil state measuring unit 132 detects a pupillary margin L1 from at least one image of images taken by the stereo camera 108, and calculates boundary coordinates of a pupil E1. The pupillary margin L1 can be detected, for example, based on the difference in luminance between the pupil E1 and an iris E2 in the image of the subject eye E.

Since in the present embodiment, the images taken by the stereo camera 108 are used, when the boundary coordinates of the pupil E1 are calculated, a visual angle (angle of view) of each of the cameras 108A and 108B is taken into consideration. In the example shown in FIG. 2 and FIG. 4, the individual cameras 108A and 108B are separated from each other and arranged substantially symmetrically in the horizontal direction (X-direction) relative to the front direction of the eye. Therefore, in order to remove deformation (distortion) in the image of the eye originated from the visual angle in the X-direction, for example, projective transformation is performed in which a trapezoidal (or quadrangular) image obtained by viewing a square from an oblique direction is transformed into a square.

Moreover, when each of the cameras 108A and 108B is disposed to be displaced in the Y-direction relative to the front direction of the subject eye E for preventing vignetting due to eyelashes and the like, the similar transformation is also performed for the Y-direction.

Here, the projective transformation on the X-direction and the projective transformation on the Y-direction may be individually performed, or synthetic transformation obtained by combining both projective transformations may be performed.

Next, the pupil state measuring unit 132 performs elliptic approximation on the boundary coordinates of the pupil to calculate the center, the major diameter and the minor diameter of a pupil approximation ellipse. First, the pupil state measuring unit 132 obtains coefficients a, b, c, d and h in the general expression ([Expression 1]) of an ellipse from the boundary coordinates of the pupil by a least squares method.

$$ax^2+by^2+cx+dy+1+hxy=0 \quad \text{[Expression 1]}$$

Next, the pupil state measuring unit 132 obtains the center coordinates of the pupil approximation ellipse from the coefficients in the general expression [Expression 1] of the ellipse. by [Expression 2].

$$(\text{Center Coordinates}) = (\overline{X}, \overline{Y}) \quad \text{[Expression 2]}$$
$$\overline{X} = \frac{hd - 2bc}{4ab - h^2}, \overline{Y} = \frac{hc - 2ad}{4ab - h^2}$$

Next, the pupil state measuring unit 132 obtains an inclination angle θ of the ellipse relative to the X-axis by [Expression 3], and obtains the axis lengths of the major axis and the minor axis of the pupil approximation ellipse. In the pupil approximation ellipse, an axis length Ax of the axis inclined by θ relative to the X-axis (hereafter referred to as the axis in the X-direction) and an axis length Ay of the axis perpendicular to the axis in the X-axis direction (hereafter referred to as the axis in the Y-direction) are obtained by [Expression 4].

$$\theta = \frac{1}{2}\tan^{-1}\left(\frac{h}{a-b}\right) \quad \text{[Expression 3]}$$

$$Ax = \sqrt{\frac{\left[(\overline{X}\cos\theta + \overline{Y}\sin\theta)^2 - \frac{1}{a}\cos^2\theta - \right]}{\left\{(\overline{X}\sin\theta - \overline{Y}\cos\theta)^2 - \frac{1}{a}\sin^2\theta\right\} \times \frac{\sin^2\theta - \frac{b}{a}\cos^2\theta}{\cos^2\theta - \frac{b}{a}\sin^2\theta}}} \quad \text{[Expression 4]}$$

$$Ay = \sqrt{\frac{\left[(\overline{X}\sin\theta - \overline{Y}\cos\theta)^2 - \frac{1}{a}\sin^2\theta - \right]}{\left\{(\overline{X}\cos\theta + \overline{Y}\sin\theta)^2 - \frac{1}{a}\cos^2\theta\right\} \times \frac{\cos^2\theta - \frac{b}{a}\sin^2\theta}{\sin^2\theta - \frac{b}{a}\cos^2\theta}}}$$

In addition to these, the pupil state measuring unit 132 calculates a displacement amount of the pupil center relative to the corneal apex (alignment reference position) obtained from the alignment index.

Figure 8:
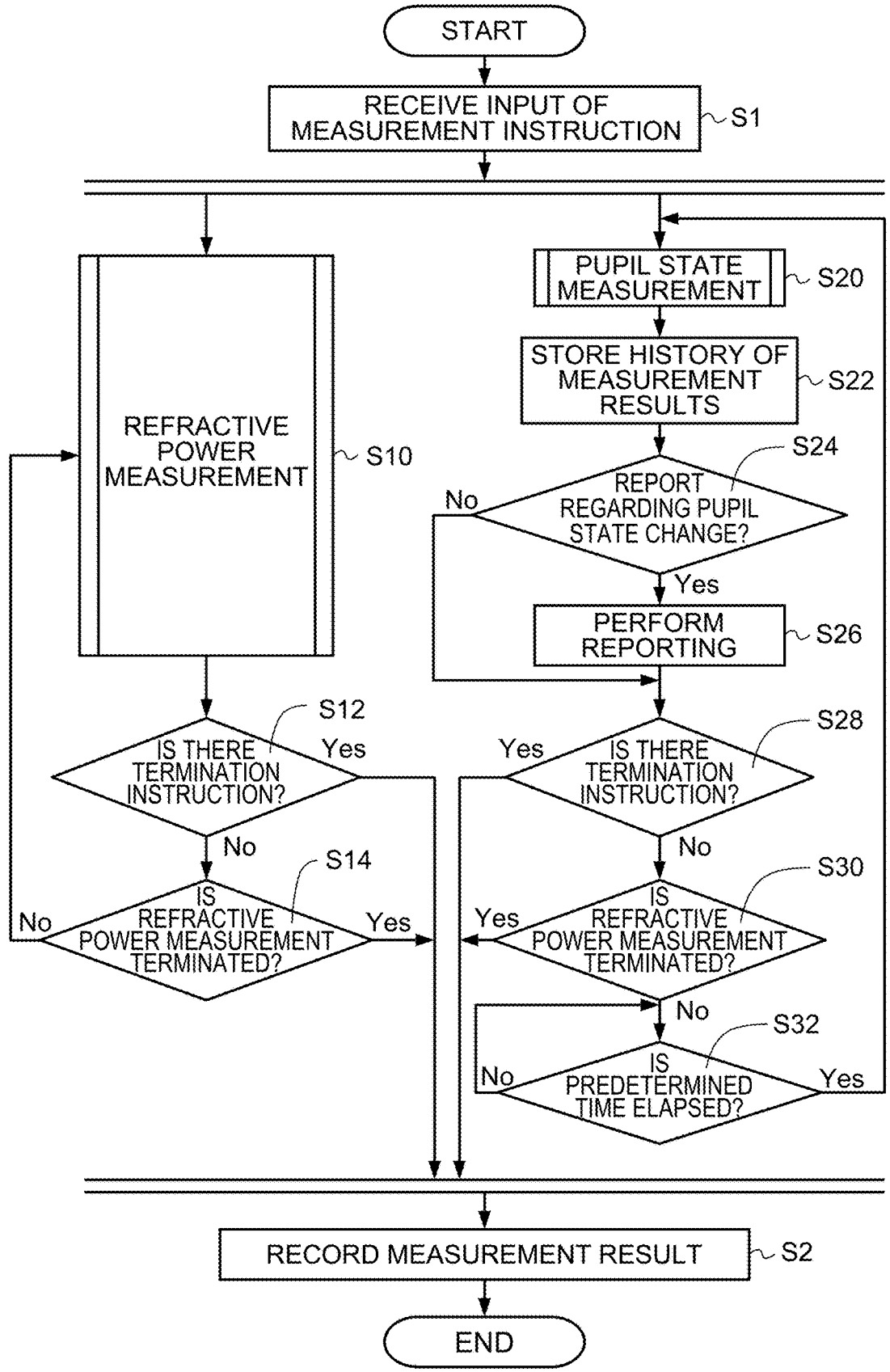
FIG. 8 is a flowchart showing a pupil state measuring method according to an embodiment of the present invention.

Next, a flow of processing of the pupil state measurement is described with reference to FIG. 8. FIG. 8 is a flowchart showing a pupil state measuring method according to an embodiment of the present invention.

While in the example shown in FIG. 8, explanation is made about an example in which the pupil state measuring unit 132 repeatedly performs a plurality of times of pupil diameter measurements during objective measurement, the present invention is not limited to this example. For example, there may be only one pupil diameter measurement, and in this case, the presence or absence of miosis and the presence or absence of eccentricity of pupil may be determined based on comparison with the reference value of the pupil diameter. The measurement results of the pupil diameter and the eccentricity may be output in a form which can be visually recognized by the optometrist, or the miosis or the eccentricity of pupil may be automatically detected by the controlling unit 122.

As shown in FIG. 8, after the completion of alignment, first, when the UI 200 receives input of an instruction for objective measurement of a refractive power of the subject eye E (step S1), objective refractive power measurement is started (step S10: refractive power measuring step), and measurement of the pupil state of the subject eye E is started (steps S20 to S32). The objective refractive power measurement and the pupil state measurement ends based on input of a termination instruction from the UI 200 (Yes in step S12 and Yes in step S28) or by the termination of the objective refractive power measurement (Yes in step S14 and Yes in step S30).

In parallel with the objective refractive power measurement (step S10), the pupil state measuring unit 132 measures the pupil state of the subject eye E for every predetermined time (for example, a millisecond to several milliseconds) (steps S20 to S30).

In step S20, first, the pupil state measuring unit 132 photographs the anterior ocular segment of the subject eye E by the cameras 108A and 108B (imaging step), and applies the projective transformation in accordance with the visual angle of each of the cameras 108A and 108B to the anterior ocular segment images. Next, the pupil state measuring unit 132 obtains the boundary coordinates of the pupil from the anterior ocular segment images after the projective transformation, performs the elliptic approximation on the pupil, and measures the pupil state by [Expression 1] to [Expression 5] (measuring step). The pupil state measuring unit 132 stores the measurement results of the pupil diameter and the eccentricity amount in the storage unit 124 (step S22).

Next, the controlling unit 122 functions as a determining unit which determines whether to issue a report regarding pupil state change or not (step S24). In step S24, the controlling unit 122 may determine to issue the report, for example, (1) when the pupil diameter on at least one longitude of the subject eye is not more than a first threshold, or (2) when the pupil diameter in the minor diameter direction is not more than the first threshold. Moreover, in step S24, the controlling unit 122 may determine to issue the report, for example, (3) when an eccentricity (displacement) of the center of pupil of the subject eye relative to the alignment reference position exceeds a reference value (second threshold). Herein, the first and second thresholds can be defined, for example, based on the diameter of a measurement luminous flux radiated onto the subject eye from the measurement optical system 112 or the similar parameter. Here, conditions for determining to issue the report or not are not limited to (1) to (3) above.

When it is determined to issue the report (Yes in step S24), the report is issued (step S26) and the process proceeds to step S28. The issuance of the report in step S26 can be performed in various ways and, for example, it may be performed by display on the display screen of the UI 200, or it may be performed using voice from a speaker.

During the objective refractive power measurement, measurement of the pupil state is repeatedly performed for every predetermined time (for example, an interval of movement of the subject eye E: several milliseconds) (step S32). Then, the measurement of the pupil state terminates when the termination instruction is input from the UI 200 (Yes in step S12 and Yes in step S28) or upon the termination of the objective refractive power measurement (Yes in step S14 and Yes in step S30). When the measurement of the pupil state terminates, the measurement result of the refractive power is stored in the storage unit 124 along with the measurement result of the pupil state (change history of the pupil state) (step S2: storing step).

In the present embodiment, a report is issued during objective refractive power measurement on the basis of the measurement result of the pupil state. However, the pupil state of the subject eye may be measured before objective refractive power measurement, and based on the measurement result, the controlling unit 122 may stop (abort) the objective refractive power measurement by the measurement optical system 112. In this case, the stop of the measurement may be reported. Or, after reporting, when operation input is received from an optometrist or the like, the measurement may be stopped. For example, in FIG. 8, before starting step S10, at least one cycle from step S20 to step S32 may be performed. Here, a determination criterion for determining whether to stop the measurement or not may be similar to that in step S24.

According to the present embodiment, it is possible to measure the pupil state of a subject eye during objective measurement, and to store the measurement result of a refractive power by the objective measurement in association with a change history of the pupil state in the objective measurement. Thereby, since the pupil state during objective measurement can be detected, accuracy of the measurement result of the refractive power by the objective measurement can be secured. Moreover, according to the present embodiment, when an error arises during objective measurement, the cause of the error can be investigated from the measurement result of the pupil state. Furthermore, according to the present embodiment, by measuring the pupil state using the two cameras 108A and 108B provided for alignment, it is possible to realize simplification and downsizing of the apparatus and cost reduction.

What is claimed is:

1. An ophthalmologic device comprising:
   an ocular characteristic measuring unit configured to objectively measure an ocular characteristic of a subject eye of a subject;
   at least two imaging units configured to substantially simultaneously photograph an anterior ocular segment of the subject eye from different directions during measurement of the ocular characteristic by the ocular characteristic measuring unit;
   a pupil state measuring unit configured to measure a pupil state of the subject eye including presence or absence of miosis, or presence or absence of eccentricity of a pupil based on at least one image of images photographed by the at least two imaging units during an objective measurement of the ocular characteristic; and
   a controlling unit configured to cause the at least two imaging units to photograph the anterior ocular segment of the subject eye, and cause the pupil state measuring unit to measure the pupil state of the subject eye based on the at least one image.

2. The ophthalmologic device according to claim 1, further comprising a distance detecting unit configured to detect a distance between the ocular characteristic measuring unit and the subject eye based on the two imaging units and the photographed images.

3. The ophthalmologic device according to claim 1, further comprising a storage unit configured to store a measurement result of the ocular characteristic by the ocular characteristic measuring unit in association with a measurement result of the pupil state, the measurement result of the pupil state having been measured by the pupil state measuring unit during the measurement of the ocular characteristic.

4. The ophthalmologic device according to claim 1, wherein the pupil state measuring unit measures, as the pupil state, at least one of a diameter of a pupil of the subject eye in each longitudinal direction and an eccentric amount of the pupil relative to a corneal apex of the subject eye.

5. The ophthalmologic device according to claim 1, wherein
   during measurement of the ocular characteristic by the ocular characteristic measuring unit, the controlling unit controls to perform photographing of the anterior ocular segment of the subject eye by the at least two imaging units and measurement of the pupil state of the subject eye based on the at least one image of the images photographed by the at least two imaging units.

6. The ophthalmologic device according to claim 1, further comprising:
   a determining unit configured to determine whether to issue a report regarding the pupil state or not, based on the pupil state of the subject eye during measurement of the ocular characteristic by the ocular characteristic measuring unit; and
   a reporting unit configured to issue the report when the determining unit determines to issue the report.

7. The ophthalmologic device according to claim 6, wherein the determining unit determines to issue the report when a pupil diameter measured by the pupil state measuring unit in at least one longitudinal direction, is not more than a first threshold determined from a diameter of a measurement luminous flux.

8. The ophthalmologic device according to claim 6, wherein the determining unit determines to issue the report when a displacement of a center position of a pupil of the subject eye relative to an alignment reference position of the pupil of the subject eye, the displacement being measured by the pupil state measuring unit, is not less than a second threshold determined from a diameter of the measurement luminous flux.

9. The ophthalmologic device according to claim 1, further comprising
   a determining unit configured to determine whether or not to perform the measurement of the ocular characteristic by the ocular characteristic measuring unit based on a pupil diameter of the subject eye before starting of the measurement of the ocular characteristic by the ocular characteristic measuring unit, wherein the controlling unit stops starting the measurement of the ocular characteristic by the ocular characteristic measuring unit when the determining unit determines not to perform the measurement.

10. The ophthalmologic device according to claim 9, further comprising a reporting unit configured to report that the measurement is not performed when the determining unit determines not to perform the measurement.

11. A pupil state measuring method comprising:
an ocular characteristic measuring step of objectively measuring an ocular characteristic of a subject eye of a subject;
a photographing step of substantially simultaneously photographing an anterior ocular segment of the subject eye from different directions using at least two imaging units during measurement of the ocular characteristic;
a measuring step of analyzing at least one image of images photographed by the at least two imaging units to measure a pupil state of the subject eye including presence or absence of miosis, or presence or absence of eccentricity of a pupil during an objective measurement of the ocular characteristic; and
a step of performing the photographing step and the measuring step during the measurement of the ocular characteristic.

12. The pupil state measuring method according to claim 11, further comprising a storing step of storing a measurement result of the ocular characteristic in association with a measurement result of the pupil state in a storage unit, the measurement result of the pupil state having been measured during the measurement of the ocular characteristic.

13. The pupil state measuring method according to claim 11, wherein the photographing step and the measuring step are repeatedly performed during the measurement of the ocular characteristic.

14. The ophthalmologic device according to claim 1, wherein the ocular characteristic measuring unit objectively measures refractive power of the subject eye of the subject as the ocular characteristic.

15. The pupil state measuring method according to claim 11, wherein refractive power of the subject eye of the subject is measured as the ocular characteristic in the ocular characteristic measuring step.

16. An ophthalmologic device comprising:
an ocular characteristic measuring unit including a light source and optical elements configured to objectively measure an ocular characteristic of a subject eye of a subject;
at least two cameras configured to substantially simultaneously photograph an anterior ocular segment of the subject eye from different directions during measurement of the ocular characteristic by the ocular characteristic measuring unit;
a pupil state processing circuit configured to measure a pupil state of the subject eye including presence or absence of miosis, or presence or absence of eccentricity of a pupil based on at least one image of images photographed by the at least two cameras during an objective measurement of the ocular characteristic; and
a controlling circuit configured to cause the at least two cameras to photograph the anterior ocular segment of the subject eye and cause the pupil state processing circuit to measure the pupil state of the subject eye based on the at least one image.

* * * * *